US010174100B1

(12) United States Patent
Deisseroth

(10) Patent No.: US 10,174,100 B1
(45) Date of Patent: Jan. 8, 2019

(54) MULTIVALENT DNA COMPOSITION FOR YERSINIA PESTIS

(71) Applicant: MicroVAX, LLC, Warrenton, VA (US)

(72) Inventor: Albert B. Deisseroth, Potomac, MD (US)

(73) Assignee: MicroVax, LLC, Warrenton, VA (US)

( * ) Notice: Subject to any disclaimer, the term of this patent is extended or adjusted under 35 U.S.C. 154(b) by 0 days.

(21) Appl. No.: 14/822,178

(22) Filed: Aug. 10, 2015

Related U.S. Application Data

(63) Continuation-in-part of application No. 13/902,025, filed on May 24, 2013, now abandoned, which is a continuation-in-part of application No. 11/593,458, filed on Nov. 6, 2006, now Pat. No. 9,533,036.

(60) Provisional application No. 61/651,145, filed on May 24, 2012.

(51) Int. Cl.
  A61K 39/00 (2006.01)
  A61K 39/02 (2006.01)
  C07K 14/24 (2006.01)
  C07K 14/705 (2006.01)

(52) U.S. Cl.
  CPC .... *C07K 14/70575* (2013.01); *A61K 39/0291* (2013.01); *C07K 14/24* (2013.01); *A61K 2039/53* (2013.01); *A61K 2039/575* (2013.01); *A61K 2039/70* (2013.01); *C07K 2319/40* (2013.01)

(58) Field of Classification Search
  None
  See application file for complete search history.

(56) References Cited

U.S. PATENT DOCUMENTS

| | | | | |
|---|---|---|---|---|
| 8,404,252 B2 * | 3/2013 | Yusibov | ............... | A61K 39/025 424/190.1 |
| 8,647,633 B2 * | 2/2014 | Heath | .................. | C07K 14/24 424/190.1 |
| 8,795,677 B2 * | 8/2014 | Heath | .................. | C07K 14/24 424/190.1 |
| 9,187,765 B2 * | 11/2015 | Rao | ...................... | C12N 15/87 |
| 9,328,149 B2 * | 5/2016 | Rao | ...................... | C07K 14/24 |
| 9,533,036 B2 * | 1/2017 | Tang | .................... | A61K 39/145 |
| 2007/0043215 A1 * | 2/2007 | Heath | .................. | C07K 14/24 536/23.5 |
| 2007/0087013 A1 * | 4/2007 | Sizemore | .......... | A61K 39/0001 424/200.1 |
| 2007/0128233 A1 * | 6/2007 | Lu | ......................... | A61K 8/25 424/401 |
| 2008/0124361 A1 * | 5/2008 | Mizel | ................. | A61K 39/0011 424/234.1 |
| 2009/0022756 A1 * | 1/2009 | Heath | .................. | C07K 14/24 424/190.1 |
| 2009/0130103 A1 * | 5/2009 | Nellis | ................ | A61K 39/025 424/134.1 |
| 2011/0027304 A1 * | 2/2011 | Yusibov | ............... | A61K 39/025 424/190.1 |
| 2012/0164156 A1 * | 6/2012 | Heath | .................. | C07K 14/24 424/164.1 |
| 2013/0034583 A1 * | 2/2013 | Stinchcomb | ......... | A61K 39/025 424/199.1 |
| 2015/0017198 A1 * | 1/2015 | Rao | ....................... | C07K 14/24 424/190.1 |
| 2016/0089427 A1 * | 3/2016 | Curtiss | .............. | A61K 39/0291 424/192.1 |
| 2016/0319322 A1 * | 11/2016 | Miller | .................. | C12Q 1/04 |
| 2017/0296644 A1 * | 10/2017 | Chopra | ............. | A61K 39/0291 |

FOREIGN PATENT DOCUMENTS

| | | | | |
|---|---|---|---|---|
| WO | WO 96/28551 | A1 | * | 9/1996 |
| WO | WO 2005/023205 | A2 | * | 3/2005 |
| WO | WO 2005/058950 | A2 | * | 6/2005 |
| WO | WO 2006/060728 | A2 | * | 6/2006 |
| WO | WO 2006/066214 | A2 | * | 6/2006 |
| WO | WO 2006/110881 | A2 | * | 10/2006 |
| WO | WO 2007/049155 | A2 | * | 5/2007 |
| WO | WO 2008/045601 | A2 | * | 4/2008 |

OTHER PUBLICATIONS

Powell et al, Biotechnol. Prog., 2005, 21:1490-1510.*
Santi et al, PNAS, USA, Jan. 24, 2006, 103/4:861-866.*
Quenee et al, Human Vaccines, Dec. 2009, 5/12:817-823.*
Goodin et al, Protein Expression and Purification, 2007, 53:63-79.*
Williamson et al, Infection and Immunity, Jun. 2005, 73/6:3598-3608.*
Anisimov et al, Infection, Genetics and Evolution, 2010, 10:137-145.*
Overheim et al, Infection and Immunity, Aug. 2005, 73/8:5152-5159.*

(Continued)

*Primary Examiner* — Nita M. Minnifield
(74) *Attorney, Agent, or Firm* — Jacob Frank; Glenn Snyder

(57) ABSTRACT

The present invention is directed to novel multivalent DNA vaccine compositions for inhibiting/blocking one or more virulence antigenic factors of *Yersinia pestis* in an individual via compositions containing fusion proteins derived from *Yersinia pestis* fused to the CD40 ligand. Specifically, it involves the administering of expression vectors carrying transcription units that encode fusion proteins comprising a *Yersinia pestis* antigenic factor fused to the aminoterminal end of the extracellular domain (ecd) of the CD40 ligand (CD40L). The first antigenic factor is a 30 amino acid region (amino acids 196-226) of LcrV outer protein and the second antigenic factor is a 127 amino acid region (amino acids 22-149) of F1 outer protein. The composition may additionally incorporate two secretable fusion proteins (amino acids 196-226 of LcrV and amino acids 22-149 of F1) or multiple antigenic factors (YpkA, YopD, YscF, YadC, OppA) in an effort to reduce the probability of immunological escape.

8 Claims, No Drawings

Specification includes a Sequence Listing.

(56) References Cited

OTHER PUBLICATIONS

Quenee et al, Vaccine, 2010, 28:1870-1876.*
Chichester et al, Vaccine, 2009, 27:3471-3474.*
Hill et al, Infection and Immunity, Apr. 2003, 71/4:2234-2238.*
Heath et al, Vaccine, 1998, 16(11/12):1131-1137.*
Guy R. Cornelis et al., "The Yersinia Yop virulon: a bacterial system for subverting eukaryotic cells", Molecular Microbiology, 1997, pp. 861-867.
Thomas Bergman et al.,"Analysis of the V Antigen IcrGVH-yopBD Operon of Yersinia pseudotuberculosis: Evidence for a Regulatory Role of LcrH and LcrV", Journal of Bacteriology, Mar. 1991, pp. 1607-1616.
S. Benson Werner et al., "Primary Plague Pneumonia Contracted From a Domestic Cat at South Lake Tahoe, Calif", JAMA, Feb. 17, 1984, vol. 251, No. 7, pp. 929-931.
Stephen T. Smiley, "Immune defense against pnuemonic plague", Immunol Rev, Oct. 2008, pp. 225, 256-271.
Jeremy L. Goodin et al.,"Purification and protective efficacy of monomeric and modified Yersinia pestis capsular F1-V antigen fusion proteins for vaccination against plague", Protein Expression and Purification 53, Dec. 31, 2006, pp. 63-79.

* cited by examiner

SEQUENCE LISTING

```
<160> NUMBER OF SEQ ID NOS: 2

<210> SEQ ID NO 1
<211> LENGTH: 38
<212> TYPE: PRT
<213> ORGANISM: Artificial Sequence
<220> FEATURE:
<223> OTHER INFORMATION: Synthetic Construct

<400> SEQUENCE: 1

Ser Glu Gln Glu Asn Cys Glu Lys Asn Leu Tyr Gly Tyr Thr Asp Glu
1               5                   10                  15

Glu Ile Phe Lys Ala Ser Ala Glu Tyr Lys Ile Leu Glu Lys Met Pro
            20                  25                  30

Gln Thr Thr Ile Gln Val
        35

<210> SEQ ID NO 2
<211> LENGTH: 155
<212> TYPE: PRT
<213> ORGANISM: Artificial Sequence
<220> FEATURE:
<223> OTHER INFORMATION: Synthetic Construct

<400> SEQUENCE: 2

Ser Glu Gln Glu Asn Cys Glu Ala Ala Thr Tyr Lys Glu Gly Ala Pro
1               5                   10                  15

Ile Thr Ile Met Asp Asn Gly Asn Ile Asp Thr Glu Ala Ala Ala Ala
            20                  25                  30

Leu Leu Val Gly Thr Leu Thr Leu Gly Gly Tyr Lys Thr Gly Thr Thr
        35                  40                  45

Ser Thr Ser Val Asn Phe Thr Asp Ala Ala Gly Asp Pro Met Ala Ala
    50                  55                  60

Ala Ala Tyr Leu Thr Phe Thr Ser Gln Asp Gly Asn Asn His Gln Phe
65                  70                  75                  80

Thr Thr Lys Val Ile Gly Lys Asp Ser Arg Asp Phe Asp Ile Ser Pro
                85                  90                  95

Ala Ala Ala Ala Lys Val Asn Gly Glu Asn Leu Val Gly Asp Asp Val
            100                 105                 110

Val Leu Ala Thr Gly Ser Gln Asp Phe Phe Val Arg Ser Ile Gly Ser
        115                 120                 125

Lys Gly Ala Ala Ala Ala Gly Lys Leu Ala Ala Gly Lys Tyr Thr Asp
    130                 135                 140

Ala Val Thr Val Thr Val Ser Asn Gln Ala Ala
145                 150                 155
```

MULTIVALENT DNA COMPOSITION FOR YERSINIA PESTIS

CROSS-REFERENCE TO RELATED APPLICATIONS

This application is a continuation-in-part of application Ser. No. 13/902,025 filed on May 24, 2013, which is a continuation-in-part of application Ser. No. 11/593,458, filed on Nov. 6, 2006, which, including all figures and tables, are both incorporated herein by reference in their entireties. Application Ser. No. 13/902,025 also claims priority and benefit under 35 U.S.C. § 119(e) of U.S. provisional patent application Ser. No. 61/651,145, filed on May 24, 2012, which, including all figures and tables, is incorporated herein by reference in its entirety.

SUMMARY OF THE INVENTION

In order to create a vaccine that will protect 100% of exposed individuals against pneumonic plague of *Yersinia pestis* (YP) by inducing "neutralizing antibodies" which promote uptake of YP by macrophages for killing of YP, and which blocks the release of exotoxins and other virulence factors by the YP cells, we have created two plasmid expression vectors encoding fusion proteins generated by the attachment of fragments of YP proteins (a 30 amino acid region (AA 196-226) of LcrV protein and a 127 amino acid region (AA 22-149) of the F1 protein) each individually to the amino terminal end of the extracellular domain of the CD40 ligand.

The vaccine strategy is novel in that the antibodies induced by the subcutaneous injection of the two plasmids or the intratracheal installation of aerosols containing these two plasmids are novel in that they do not block binding of the infectious agent to target cells, but block and suppress virulence functions of the YP. The first novel mechanism of the neutralizing antibody is to coat the YP F1 virulence protein thereby inactivating it. The F1 normally blocks uptake of YP into macrophages where the YP cells are killed by macrophage functions. The neutralizing antibodies, instead of preventing uptake of the infectious agent, actually promote uptake of YP into macrophages (the opposite of the way most neutralizing antibodies work).

The second novel mechanism is that the neutralizing antibodies induced by the vaccine coat the LcrV protein, the function of which is essential to the secretion of other virulence factors by the YP once it is taken up into the macrophage which result in the death of the macrophage.

Thus, a novel vaccine strategy (blocking of virulence functions of YP) result in the uptake and killing of the YP cells by the macrophage. This vaccine is unique in its composition of matter, its structure, and by the strategy with which it stops a YP infection from happening. This is the first time such a strategy has been developed.

FIELD OF THE INVENTION

The present invention relates generally to the field of vaccines and antimicrobial prophylaxis. More specifically, it is directed to novel multivalent DNA vaccine compositions and methods of inhibiting/blocking one or more virulence antigenic factors of *Yersinia pestis* via formulations containing fusion proteins derived from *Yersinia pestis* fused to the CD40 ligand.

BACKGROUND OF THE INVENTION

The following discussion of the background of the invention is merely provided to aid the reader in understanding the invention and is not admitted to describe or constitute prior art to the present invention.

*Yersinia pestis* (YP), a facultative anaerobe, is a Gram-negative *bacillus*. It is the etiological agent of plague, a zoonotic disease usually transmitted to humans from infected rodents via the bite of an infected flea. YP infection can result in three forms of the disease: (i) bubonic, (ii) septicemic and/or (iii) pneumonic plague. Pneumonic plague is highly contagious and easily transmitted among humans via airborne droplets, resulting in a rapid onset of disease and a mortality rate approaching 100% if treatment is delayed more than 24-hour postexposure.

Recently, plague has attracted a considerable attention because of its potential misuse as a biological warfare agent. The US Centers for Disease Control and Prevention regards *Yersinia pestis* as a type A bioterrorism threat. Most experts agree that a large plague outbreak would put health-care resources under severe pressure given the disease's inherent communicability, rapid clinical course, and high mortality if left untreated. Thus, it is imperative to develop an ideal plague vaccine for human use.

Historically, plague was a fatal infectious disease afflicting human populations, leading to millions of deaths. *Yersinia pestis* infections have led to three great pandemics that have caused the deaths of millions of individuals throughout history. The first was in the Mediterranean area in the $5^{th}$ to $6^{th}$ centuries AD, and the second was in Europe between the 8th and 14 centuries AD, both killing about one-half of the existing population. The third started in China in the 19th century and is still ongoing. The disease is transmitted to human beings from animals (cats and rats) by the infected fleas that they carry. Human to human transmission can occur through contact with the bodily fluids or aerosols produced by late stage infected individuals (1). Because millions of animals are infected worldwide in deserts, the steppes, mountains and forest (2), this disease will probably never be eradicated. Although there are antibiotics for treatment of these infections, the mortality is still high due to the rapid rate of the spread of the infection, once it is established in a human subject. There continue to be isolated, sporadic outbreaks of infections within the United States and around the world: (a) the 1994 plague outbreak from India; (b) the death of a woman in 1984 in the Lake Tahoe area who contracted the disease from her cat (3); (c) A case of bubonic plague in a 58 year old man was reported in 2011 in New Mexico; and (d) ground squirrels infected with the plague were recently reported in the San Diego area.

To date, there are no approved vaccines for *Yersinia pestis*. It is still very difficult to protect against pneumonic plague induced by inhalation of contaminated aerosols using vaccination. Accordingly, YP remains a bioterrorist threat for which there is no satisfactory countermeasure. YP is capable of spreading very rapidly in a human subject because of the *Yersinia* Outer Proteins (Yops) which block the immune response against YP, and kill the cells into which YP is taken up (4-5). One of these Yops is LcrV, a 41-kDa protein that is at the tip of the type III needle translocation complexes, and is required for the secretion of two other Yops: YopB and YopD (6-7). Another of these Yops is F1, the capsular pilus antigen that covers the outer wall of YP (8-9), and thereby prevents the uptake and killing of YP by macrophages (8). LcrV is involved in translocation of toxins from the YP bacterial cell to the cytoplasm of the YP infected host cell and F1 is a protein on the outer surface of YP that prevents phagocytosis of YP by macrophages (5). These two proteins are important to the virulence of YP since the administration of antibodies to these two proteins (singly or in combination) can protect mice from the effects of lethal doses of YP (10). Antibodies to these two proteins interact synergistically in protecting mice from YP challenge (10-11). While LcrV is required for virulence, F1 is dispensable (11-12).

DETAILED DESCRIPTION OF THE INVENTION

In this specification, although the preferred embodiments have been described in detail, it should be understood that various changes, substitutions and alterations might be made therein without departing from the spirit and scope of the invention. Therefore, the specification is to be regarded in an illustrative rather than a restrictive sense.

Furthermore, all references, including publications, patent applications and patents, cited herein are incorporated by reference in full to the same extent as if each individual publication was specifically and individually indicated to be incorporated by reference. They are indicative of the levels of those of ordinary skill in the art to which the invention pertains and may be employed in the practice of the instant invention.

1. DEFINITIONS

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the terms "antigen" or "antigenic factors" refers broadly to any antigen to which a human, mammal, bird or other animal can generate an immune response. The terms "antigen" or "antigenic factors" as used herein refers broadly to a molecule that contains at least one antigenic determinant to which the immune response may be directed. The immune response may be cell-mediated, humoral or both. As is well known in the art, an antigen may be protein, carbohydrate, lipid, or nucleic acid or any combinations of these biomolecules. As is also well known in the art, an antigen may be native, recombinant or synthetic. For example, an antigen may include non-natural molecules such as polymers and the like. Antigens include both self-antigens and non-self antigens. As used herein, "antigenic determinant" (or epitope) refers to a single antigenic site on an antigen or antigenic factor; it is a minimal portion of a molecule that recognized by the immune system, specifically by antibodies, B cells or T cells. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein is an amount that results in an increase in the immune response as measured by an increase in T cell activity or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr]-MDP (Byersand Allison, *Vaccine* 5:223 (1987)), monophosphoryl lipid A (Johnson et al., *Rev. Infect. Dis.* 9:S512 (198)), and the like.

The term "vector" as used in this application contains a transcription unit (also known as an "expression vector"). It encompasses both viral and non-viral expression vectors that when administered in vivo can enter target cells and express an encoded protein. Viral vectors have evolved means to overcome cellular barriers and immune defense mechanisms. Viral vectors suitable for in vivo delivery and expression of an exogenous protein are well known in the art and include adenoviral vectors, adeno-associated viral vectors, retroviral vectors, vaccinia vectors, pox vectors, herpes simplex viral vectors, etc. Viral vectors are preferably made replication defective in normal cells. For example, see U.S. Pat. Nos. 6,669,942; 6,566,128; 6,794,188; 6,110,744 and 6,133,029. On the other hand, nonviral gene carriers consistently exhibit significantly reduced transfection efficiency as they are hindered by numerous extra- and intracellular obstacles. Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture is useful as a vehicle for non-viral expression vectors. See U.S. Pat. No. 6,147,055. Polycation-DNA complexes also may be used as a nonviral gene delivery vehicle. See Thomas et al., *Appl Microbiol Biotechnol* (2003) 62(1):27-34. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously.

The term "transcription unit" as used herein in connection with an expression vector means a stretch of DNA, that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element (s). A useful promoter/enhancer is the cytomegalovirus (CMV) immediate-early promoter/enhancer. See U.S. Pat. Nos. 5,849,522 and 6,218,140.

The term "secretory signal sequence" (also known as "signal sequence," "signal peptide," leader sequence, "or leader peptide") as used herein refers to a short peptide sequence, generally hydrophobic in charter, including about 20 to 30 amino acids that is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments, the endogenous tumor antigen signal sequence also may be used to direct secretion.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that block *Yersinia pestis* (also see section 8).

The term "linker" as used employed in this application with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See, e.g. Arai et al. Protein Engineering, Vol. 4, No. 8, 529-532, August 2001). In certain embodiments of the present invention, the linker is from about 3 to about 15 amino acids long, more preferably from about 5 to about 10 amino acids long. However, longer or shorter linkers may be used or the linker may not be used at all. Longer linkers may be up to about 50 amino acids, or up to about 100 amino acids. One example of a linker well known in the art is a 15 amino acid linker consisting of three repeats of four glycines and a serine (i.e., [Gly$_4$Ser$_3$)].

2. LIST OF ABBREVIATIONS

Some of the abbreviations used in the instant application appear below:

YP—*Yersinia pestis*
Yops—*Yersinia* Outer Proteins
LcrV—Low Calcium Response V Antigen
F1—Fraction 1 Antigen
Ad—Adenoviral
Sig—signal sequence
TAA—Target Associated Antigen
ET—epitopic target
ecd—extracellular domain
SC—subcutaneous or subcutaneously
CD40L—CD40 ligand
CMV—Cytomegalovirus
PA—Protective Antigen
EF—Edema Factor
LF—Lethal Factor

3. GENERAL DESIGN OF THE INVENTOR'S TAA/ECDCD40L VACCINE PLATFORM

Some of the factors that limit response to *Yersinia pestis* are (i) immunodeficiency (13-18), (ii) debilitation from chronic diseases, (iii) a lack of prior exposure, and (iv) low immunogenicity of the *Yersinia pestis* antigens.

The inventor's laboratory (19-27) has developed a TAA/ecdCD40L vaccine platform that is specifically designed to overcome the defective response to vaccination in immunosuppressed, debilitated patients who are of advanced chronological age, and to increase the potency of weak antigens as immunogens to increase the titer of neutralizing antibodies induced by the vaccine (25). The basis for the success of this vaccine is that it supplies a potent specific immunostimulatory signal (namely, ecdCD40L) that amplifies the magnitude of the immune response induced by vaccine, and provides a signal that is missing in older individuals, thereby diminishing the response of older individuals to vaccination (17-18). Either this vaccine is customarily given subcutaneously as a TAA/ecdCD40L protein or in an expression vector that has a TAA/ecdCD40L transcription unit (19-27).

There are three versions of this TAA/ecdCD40L vaccine:
1. one in which the TAA/ecdCD40L transcription unit is embedded in a replication incompetent adenoviral vector (Ad-sig-TAA/ecdCD40L) which is injected subcutaneously (SC) used as an initial priming injection, followed by two SC injections of the TAA/ecdCD40L protein;
2. one in which the vaccine consists solely of the TAA/ecdCD40L protein that is injected SC; and
3. one in which the TAA/ecdCD40L is encoded in a DNA plasmid which is injected intramuscularly (IM).

In order to create a vaccine that can induce high titers of neutralizing antibodies even against antigens which are weakly immunogenic (such as the LcrV and F1 target associated antigens (TAA of YP)), the inventor's laboratory has designed the TAA/ecdCD40L vaccine platform in which the TAA is connected to the amino-terminus of the extracellular domain (ecd) of the potent immunostimulatory signal, CD40 ligand (CD40L). This attachment of the TAA to the ecdCD40L accomplishes two things:
(1) The binding of the TAA/ecdCD40L protein to the CD40 receptor on the dendritic cells (DCs) as well as on the B cells and T cells, activates these cells thereby replacing the CD40L signal, which is missing on the plasma membrane of the CD4 helper T cells of older individuals (5-6).
(2) Once the TAA/ecdCD40L protein binds to the CD40 receptor of the DC, the entire TAA/ecdCD40L protein is internalized into the DC in a way that allows the TAA to be processed through the Class I as well as the Class II MHC presentation pathways (16-24). CD40L is also necessary for the activation of the secondary signals on the dendritic cells that promotes a potent, and sustained adaptive immune response. Then, the activated TAA-loaded DCs migrate to the regional lymph nodes (20) where they can activate and induce expansion of the TAA specific CD8 effector T cells and B cells that make TAA specific antibodies. These antigen-specific CD8 effector cells increase in number in the lymph nodes (16-18), and then egress from the lymph nodes into the peripheral blood. The antigen specific CD8 effector T cells exit the intravascular compartment and enter into the extravascular sites of inflammation or infection 9. In addition to showing that this vaccine increases the antigen specific CD8 effector T cells in the sites of inflammation, we have shown that the activation and expansion of the B cells by the TAA/ecdCD40L protein increases the levels of the TAA specific antibodies in the serum (19-27).

The inventor has demonstrated that the activation and expansion of TAA specific B and T cells induced by the TAA/ecdCD40L vaccine increases the levels of the TAA specific antibodies in the serum as well as the levels of TAA specific CD8 effector T cells in the sites of tissue inflammation (22). The inventor's experiments have shown that the TAA/ecdCD40L vaccine induces memory for over a year (19), and converts weak immunogens into strong or potent immunogens in younger as well as in older or immunodeficient test subjects (25). The TAA/ecdCD40L vaccine has been observed to induce titers up to 1/4000 for some viral antigens (25). Such vaccines have a long shelf life (>5 years when stored frozen).

4. BACKGROUND ON POOR RESPONSE TO VACCINE AMONG IMMUNODEFICIENT INDIVIDUALS

The response to vaccination, in general, may be limited by several factors such as (i) low immunogenicity of the target antigen; (ii) the state of health and the age of the individual; (iii) chronic infections or cancer; or (iv) other host factors that lead to defective function of CD8 T cells, CD4 T cells, B cells, and dendritic cells (DCs). The inventor has found that the linkage of the target antigen or a piece of the target antigen the immune response to the vaccine in young as well as older test subjects. This vaccine strategy makes weak antigens strong and potent immunogens, and overcomes states of anergy due to central or peripheral tolerance. This is due to the fact the engagement of the CD40 receptor on antigen specific B and CD8 T cells by the CD40L on the surface of CD4 helper T cells is an essential step for these cells to expand in number in response to vaccination, the loss of expression of CD40L in the activated CD4 helper T cells of older individuals. The loss of presentation of the CD40L in the CD4 helper T cells of older individuals is an example of the importance of the presence of the CD40L in the immune response.

In some immunodeficient (e.g., debilitated or older individuals), the absence of the presentation of the CD40L on activated CD4 helper T cells reduces the magnitude of the immune response to influenza vaccination. Recent analyses of human influenza vaccination clinical data show that less than 20% of individuals above 55 years of age develop a fully protective neutralizing antibody response to the yearly multivalent particle inactivated human influenza vaccine (10-13). This is due to the acquisition of both quantitative as well as qualitative defects such as loss of expression of CD40 ligand (CD40L) on CD4 helper T cells during activation (14-15) in the immune response as individuals reach the 5th and 6th decades of life.

5. APPLICATION OF VACCINE PLATFORM TO INFLUENZA TO CONVERT WEAK ANTIGENS INTO STRONG ANTIGENS EVEN IN IMMUNODEFICIENT INDIVIDUALS

The inventor has previously established (25) that the HA/ecdCD40L vaccine and the M2/ecdCD40L vaccine, where HA and M2 are derived from the A/Hong Kong/156/97 avian influenza virus, dramatically increases the levels of both HA and M2 specific splenic CD8 T cells as well as HA and M2 specific antibodies even is aged test mice. The levels of the response induced in old as well as young mice to avian M2, which is a weak immunogen, by the M2/ecdCD40L vaccine are equivalent to the levels of hemagglutinin (HA) specific CD8 T cells and serum antibodies induced by the HA/ecdCD40L vaccine (where HA is also derived from the A/Hong Kong/156/97 virus). The response to previous vaccines involving M2 flu antigens in a viral particle or as a recombinant protein is historically much weaker than to vaccines involving HA. Thus, it appears that the linkage of the M2 antigen to CD40L has not only overcome the defect in CD4 helper T cell function among older test subjects, but it has also dramatically increased the immunogenicity of weak viral antigens.

6. STRUCTURE OF THE *YERSINIA PESTIS* TAA/ECDCD40L VACCINE

Mouse monoclonal antibodies to LcrV and F1 antigenic factors were capable of protecting test mice against infections with *Yersinia pestis* (10). In order to create the instant *Yersinia pestis* pneumonic plague vaccine that induces high levels of neutralizing antibodies and offers protection of 100% of the test animals or subjects, the present invention proposes to create a multivalent DNA vaccine effective against *Yersinia pestis* composed of an expression vector carrying transcription units which encode fusion proteins comprising a *Yersinia pestis* antigenic factor (TAA) fused to the aminoterminal end of the extracellular domain (ecd) of the CD40 ligand (CD40L). In this novel construct, the first antigenic factor is a 30 amino acid region (amino acids 196-226) of LcrV outer protein (6-7, 11-12); and the second antigenic factor is a 127 amino acid region (amino acids 22-149) of F1 outer protein (8-9). The inventor has designated the plasmids containing the expression vectors as pCMV-sig-LcrV$_{196-226}$/ecdCD40L and pCMV-sig-F1$_{22-149}$/ecdCD40L respectively.

In a preferred embodiment of the instant invention, the vaccine composition may further include an effective amount of two secretable fusion proteins, wherein each fusion protein comprises a *Yersinia pestis* antigenic factor and CD40 ligand, and wherein said first antigenic factors is a 30 amino acid region (amino acids 196-226) of LcrV outer protein and the second antigenic factor is a 127 amino acid region (amino acids 22-149) of F1 outer protein. The amino acid sequence (7) of the 30 amino acid region (amino acids 196-226) of LcrV outer protein is as follows which is SEQ ID NO. 1):

(SEQ ID NO. 1)
KNLYGYTDEEIFKASAEYKILEKMPQTTIQV

The amino acid sequence (9) of the 127 amino acid region (amino acids 22-127) of the F1 protein is as follows (which is SEQ ID NO. 2):

```
                                        (SEQ ID NO. 2)
AA22-TYKEGAPITIMDNGNIDTE-AA40

AA41-LLVGTLTLGGYKTGTTSTSVNFTDAAGDPM-AA70

AA71-YLTFTSQDGNNHQFTTKVIGKDSRDFDISP-AA100

AA101-KVNGENLVGDDVVLATGSQDFFVRSIGSKG-AA130

AA131-GKLAAGKYTDAVTVTVSNQ-AA149
```

The instant vaccine composition may be administered intramuscularly, subdermally, mucosally (orally, rectally, or intranasally) or subcutaneously as a single dose or as multiple doses. The vaccine has the ability to generate a humoral and cellular immune response, thereby blocking the binding of the bacterium to cellular receptors or interfering with the assembly of infective bacterium. The perceived advantages of the instant invention are that the vaccine is effective in reducing the extent of tissue damage by *Yersinia pestis* and imparting immune memory function against *Yersinia pestis*.

7. SELECTION OF *YERSINIA PESTIS* ANTIGENIC FACTORS

During vaccine formulation, fragments or regions (i.e., antigenic factors) of F1 or LcrV of *Yersinia pestis* are selected which are from locations in these two proteins which are known to be key to their functions (criterion #1) and bind to Class I MHC or Class II MHC (criteria #2-3). Furthermore, multiple antigens may be selected to reduce the probability of immunological escape. In this regard, additional *Yersinia pestis* antigenic factors (such as, YpkA, YopD, YscF, YadC, OppA) can be additionally incorporated into the vaccine formulation so that the probability of immunological escape is reduced (see section 10).

8. ADVANTAGES OF THE INVENTOR'S *YERSINIA PESTIS* VACCINES

As discussed earlier, LcrV and F1 are "outer proteins" of *Yersinia pestis* that contribute to the virulence, rapid progression of *Yersinia pestis* infection and blocking of the immune response to *Yersinia pestis*. The inventor's multivalent DNA vaccines would induce high titers of neutralizing antibodies that would block the function of the LcrV and F1 proteins, the two important virulence factors that limit the ability of human subjects to respond immunologically to *Yersinia pestis* infections. These vaccines would therefore completely protect all individuals in a population, even those debilitated or immunosuppressed by chronic disease, or of advanced chronological age. Furthermore, inclusion of additional *Yersinia pestis* antigenic factors (YpkA, YopD, YscF, YadC, OppA) into the vaccine formulation will be effective against mutant strains or bio-weaponized varieties, thereby reducing the probability of immunological escape.

In this regard, the induction of neutralizing antibodies and CD8 effector T cells against *Yersinia pestis* proteins (antigenic factors) can have the following effects:

(a) block the function of LcrV on which the secretion of other *Yersinia pestis* virulence factors depends;
(b) block the function of F1 that will then result in an increased uptake and killing of *Yersinia pestis* by host macrophages;
(c) induce high levels of *Yersinia pestis* specific antibodies and CD8 effector T cells;
(d) prevent of the establishment of an infection by *Yersinia pestis*;
(e) limit the extent of tissue damage by *Yersinia pestis*; and
(f) impart a memory function.

It should be pointed out that there is a distinction between the functionality of the neutralizing antibodies that are induced to the influenza antigen Hemagglutinin (HA) versus the neutralizing antibodies proposed by the inventor and the subject of the instant invention against the *Yersinia pestis* F1. The influenza virus must enter mammalian cells in order to replicate itself which it accomplishes via the HA protein, a stalk-like structure which extends out from the capsid protein like a spike. The end of the HA is called the "knob" which binds to the cell by fitting inside of a cellular receptor. Once it binds, it is taken up into the cell by endocytosis. Neutralizing antibodies to the knob region of the HA impede the binding of the HA to its cellular receptor and thereby render the influenza virus non-infective. If the titer of the neutralizing antibodies is high enough, the amplification of the virus inside the body of the infected host stops. The neutralizing antibodies stop influenza infection by preventing uptake of the virus via mammalian cells. On the other hand, in the case of *Yersinia pestis* F1, the function of this protein is to impede and prevent the uptake of the bacterial cell by the macrophage that leads to intracellular killing of the *Yersinia pestis* bacterial cell. The neutralizing antibodies generated against F1 bind to F1 and block the ability of F1 to prevent uptake by macrophages. Thus, the neutralizing antibody to F1 promotes uptake of the infectious agent into mammalian cells (i.e., macrophages) by inhibiting or "neutralizing" the function of F1, thereby inhibiting or blocking *Yersinia pestis* pathogenesis.

9. VACCINE DELIVERY VIA AEROSOL INHALATION

A preferred embodiment of the invention involves delivery of the vaccine formulation as an aerosol in order to induce resistance to pneumonic plague. The rationale for this approach is discussed below.

Some immunologists feel that when an infection is initiated in a particular location in the body (such as lung tissue), the resident dendritic cells take up the antigens, cross present them, and migrate to the regional lymph nodes where they find antigen specific CD8 effector T cells and antigen specific B cells which are then activated and expanded in number. The CD8 effector T cells then leave the lymph nodes, go into the blood and then tend to be attracted by chemokine receptor/ligand interactions or cytokine gradients in the infected tissue or the tissue site of the vaccine injection. Choosing the inhalation route for vaccination ensures that the CD8 effector T cells, which are antigen specific, will home to the lung tissue and invade the lung parenchyma where they will kill lung cells that have already taken up *Yersinia pestis*, or release cytokines which attract macrophages that kill *Yersinia pestis* via ingestion and intracellular killing. The antibodies directed to F1 or LcrV will go all over the body. Thus, the inhalational route is important in attracting cells of the immune response to the lung tissue and to activating the alveolar macrophages to ingest *Yersinia pestis*.

Accordingly, in order to get complete protection, any one or all of these may be employed in an aerosol delivery: (i) plasmids (pCMV-sig-LcrV$_{196-226}$/ecdCD40L and pCMVsig-F1$_{22-170}$/ecdCD40L) carrying transcription units which encode the fusion proteins as the vaccine formulation; (ii) a protein vaccine containing the fusion proteins; or (iii) an adenoviral vaccine which encodes the fusion proteins (LcrV$_{196-226}$/ecdCD40L and F1$_{22-170}$/ecdCD40L) to increase the potency of the immune response over that possible with the antigen alone (unattached to ecdCD40L).

10. STRATEGY TO COUNTER A BIOTERRORIST'S ATTEMPT TO "WEAPONIZE" YERSINIA PESTIS

Because it is common knowledge that the F1 and LcrV proteins are targets for neutralizing antibodies which block the functions of F1 and LcrV, a bioterrorist lab could theoretically try to weaponize Yersinia pestis by altering or removing the antigenic factors which are the targets of the neutralizing antibodies for F1 and LcrV, without reducing the virulence of the Yersinia pestis bacterial cell. This would then circumvent attempts of the US government to protect high-risk individuals through vaccination with antigens from F1 and LcrV. The bioterrorist may be accomplish this by systemically searching for mutations (amino acid substitutions) within F1 or LcrV that make them immunologically unrecognizable by neutralizing antibodies yet do not reduce their virulence. In fact, it is well known that there are strains of Yersinia pestis that contain LcrV with different amino acid sequence yet retain the function of LcrV.

Hence, to counter this bioterrorist strategy, the inventor contemplates increasing the number of antigenic factors of Yersinia pestis from the two that have been proposed (F1 and LcrV linked to ecdCD40L), to creating fusion proteins by attaching ecdCD40L to the following antigenic factors of Yersinia pestis: YpkA, YopD, YscF, YadC, and OppA. Fusion proteins containing these additional antigenic factors could then be additionally incorporated in the vaccine formulation along with the other two antigenic factors (F1 and LcrV linked to ecdCD40L). This strategy would be similar in principle to the strategy the inventor has previously claimed in order to reduce the probability of immunological escape by increasing the number of antigens.

11. REFERENCES CITED

1. Kool J L. Risk of person-to person transmission of pneumonic plague. *Clinical Infectious Diseases* 40: 1166-1172, 2005.
2. Dufel A E. Plague. Medscape Drugs, Diseases and Procedures. http://emedicine.,medscape.com/article 829233-overview. May 22, 2013.
3. Werner S B, Weidmer C E, Nelson B C, Nygaard G S, Goethals R M, and Poland J D. Primary plague pneumonia contracted from a domestic cat at South Lake Tahoe, C A. *JAMA* 17: 929-931, 1984.
4. Cornelis G R, and Wolf-Watz H. The Yersinia Yop virulon: a bacterial system for subverting eukaryotic cells. *Molecular Microbiology* 23: 861-867, 1997.
5. Smiley S T. Immune defense against pneumonic plague. *Immunological Reviews.* 225: 256-271, 2008.
6. Sarker M R, Neyt C, Stainier I, and Cornelis G R. The Yersinia Yop Virulon: LcrV is required for extrusion of the translocators YopB and YopD. Journal of Bacteriology 180: 1207-1214, 1998.
7. Bergman T, Hakansson S, Fosberg A, Norlander L, Marcellaro A, Baackman A, Bolin I, and Wolf-Watz H. Analysis of the V antigen lcfGVH-yopBD operon of Yersinia pseudotuberculosis (and comparison with that of Y pestis): evidence for a regulator role of LcfH and LcfV. J Bacteriology 173: 1607-1616, 1991.
8. Chichester J A, Musiychuk K, Farrance C E, Mett V, Lyons J, Mett V, Yusibov, V. A single component two-valent Lcrv-F1 vaccine protects non-human primates against pneumonic plague. Vaccine 27: 3471-3474, 2009.
9. Goodin J L, Nellis D F, Powell B S, Vyas V V, Enama J T, Wang L C, Clark P K, Giardina S L, Adamovicz J J, and Michiel D F. Purification and protective efficacy of monomeric and modified Yersinia pestis capsular F1-V antigen fusion proteins for vaccination against plague. Protein Expression and Purification 53: 63-79, 2007.
10. Hill J, Copse C, Leary S, Stagg A J, Williamson E D, and Titball R W. Synergistic protection of mice against plague with monoclonal antibodies specific for the F1 and V antigens of Yersinia pestis. *Infection and Immunity* 71: 2234-2238, 2003.
11. Quenee L E, and Schneewind O. Plague vaccines and the molecular basis of immunity against Yersinia pestis. *Human Vaccine* 5: 817-823, 2009.
12. Quenee L E, Berube B J, Segal J, Elli D, Ciletti N A, Anderson D, and Schneewind O, Amino acid residues 196-225 of LcrV represents a plague protective epitope, Vaccine 2010 Feb. 17; 28(7): 1870. doi:10.1016/j. vaccine.2009.11.076.
13. Jefferson T, Rivetti D, Rivetti A, Rdin M, Di Pietrantonj C, and Demicheli V. Efficacy and effectiveness of influenza vaccines in elderly people: a systematic review. *Lancet* 366, 1165-1174, 2005.
14. Goodwin K, Viboud C, and Simonsen L. Antibody response to influenza vaccination in the elderly: a quantitative review. *Vaccine* 24, 1159-1169, 2006.
15. Simonsen, L et al. Mortality benefits of influenza vaccination in elderly people: an ongoing controversy. *Lancet Inf. Dis* 7: 658-666, 2007.
16. Jackson M L et al. Influenza vaccination and risk of community-acquired pneumonia in immunocompetent elderly people: a population-based, nested case-control study. *Lancet* 372: 398-405, 2008.
17. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. *Journal of General Virology* 84, 1623-1628, 2003.
18. Eaton S M et al. Age-related defects in CD4 T cell cognate helper function lead to reductions in humoral responses. *J. Exp. Med.* 200: 1613-1622, 2004.
19. Zhang L, Tang Y, and Deisseroth A: Adenoviral vectors encoding a secretable HPV 16 E7/CD40 ligand fusion protein induce immunity for up to one year in a murine model. *PNAS,* 100: 15101-15106, 2003.
20. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. *Blood,* 104: 2704-2713, 2004.
21. Akbulut H, Tang Y C, Maynard J, and Deisseroth A. Dendritic cells improve the efficacy of vector targeted chemotherapy in breast cancer. *Molecular Cancer Therapeutics* 5: 1975-1985, 2006.
22. Tang, Y C, Maynard J, Akbulut H, Fang X M, Zhang W W, Xia X Q, Koziol J, Linton P J, and Deisseroth. Vector Prime/Protein Boost Vaccine Which Overcomes Defects Acquired During Aging and Cancer. *J. Immunology,* 177: 5697-5707, 2006.

23. Tang Y, Akbulut H, Maynard J, Zhang L, Petersen L, and Deisseroth A. Vaccine strategies for cancer and infectious diseases in the elderly. Gene Therapy 2007, Edited by T. Ochiai, H. Shimada, and M. Tagawa, Chiba, Japan, pp. 78-85, 2007.
24. Akbulut H, Tang Y C, Maynard J, and Deisseroth A. Chemotherapy targeted to cancer tissue potentiates antigen specific immune response induced by vaccine for antigen loading and activation of dendritic cells. *Molecular Therapy*, 10: 1753-1760, 2008.
25. Tang, Y C, Linton, P J, Thoman M, and Deisseroth A. Symposium in Writing: Vaccine for Infections and Cancer. *Cancer Immunology Immunotherapy* 58: 1949-1957, 2009.
26. Han T H, Park Y H, Maynard J, Li P C, Tang Y C, and Deisseroth A. Vector prime protein boost vaccination in the setting of myeloablative-induced lymphopenia suppresses growth of leukemia and solid tumors. *Bone Marrow Transplant.* 45(3): 550-557, 2010.
27. Akbulut H, Tang Y C, Akbulut G, Maynard J, and Deisseroth A. Vaccine combined with vector targeted chemotherapy reduces levels of cancer stem cells and improves outcome of cancer treatment, *Gene Therapy* 17: 1333-1340, 2010.

I claim:

1. A multivalent DNA composition comprising: (i) a mixture of expression vectors each carrying one of two transcription units each of which transcription units encodes a different one of two distinct fusion proteins, each of which fusion proteins comprises a fragment of the *Yersinia pestis* outer protein antigenic factor fused to the aminoterminal end of the extracellular domain (ecd) of the CD40 ligand (CD40L), wherein a first antigenic factor of a first one of said two fusion proteins is a 30 amino acid region fragment SEQ ID NO. 1 of the LcrV outer protein and a second antigenic factor of a second one of said two fusion proteins is a 127 amino acid region fragment SEQ ID NO. 2 of the F1 outer protein; (ii) one or more adjuvants; and (iii) one or more pharmaceutically acceptable carriers, wherein each of said fusion proteins has the ability to generate antigen specific CD8 effector T cells and antigen specific neutralizing antibodies against one or more *Yersinia pestis* antigenic factors.

2. The composition of claim 1, administered via a delivery method selected from a group comprising intramuscular, mucosal, subdermal, subcutaneous, and combinations thereof, wherein said administration is as a single dose or as multiple doses.

3. The composition of claim 1, wherein said composition has the ability to generate a humoral and cellular immune response, thereby blocking the binding of the bacterium to cellular receptors or interfering with the assembly of infective bacterium.

4. The composition of claim 1, wherein said each antigenic factor and CD40 ligand are covalently linked.

5. The composition of claim 1, wherein said CD40 ligand is human CD40 ligand.

6. The composition of claim 1, wherein said CD40 ligand is missing its transmembrane domain.

7. The composition of claim 1, wherein said expression vector is a plasmid DNA or viral vector.

8. The composition of claim 1, wherein said expression vectors are adenoviral vectors.

\* \* \* \* \*